(12) United States Patent
Benedyk (10) Patent No.: US 6,489,350 B1
(45) Date of Patent: Dec. 3, 2002

(54) METHODS FOR TREATING NEUROPATHIC PAIN USING HETEROARYLMETHANESULFONAMIDES

(75) Inventor: Mark J. Benedyk, San Diego, CA (US)

(73) Assignee: Elan Pharmaceuticals, Inc., South San Francisco, CA (US)

(*) Notice: Subject to any disclaimer, the term of this patent is extended or adjusted under 35 U.S.C. 154(b) by 0 days.

(21) Appl. No.: 09/663,107

(22) Filed: Sep. 15, 2000

Related U.S. Application Data (60) Provisional application No. 60/153,939, filed on Sep. 15, 1999.

(51) Int. Cl.[7] .................. A61K 31/423; A61K 31/42
(52) U.S. Cl. ............................. 514/375; 514/379
(58) Field of Search ................................ 514/375, 379

(56) References Cited

PUBLICATIONS

Morimoto et al., Pein Kurinikku (Pain Clinic), vol. 18, No. 7, pp. 936–940 (1997) (abstract).*
Owen et a., Brain Res., 770/1,2, pp. 115–122 (abstract), 1997.*
Morimoto et al., Pein Kurinikku, 19/6, pp. 901–903, 1998.*

* cited by examiner

*Primary Examiner*—Phyllis G. Spivack
(74) *Attorney, Agent, or Firm*—J. Mark Hoch

(57) ABSTRACT

A method of treating neuropathic pain and its progression is disclosed comprising administering to a subject a compound of formula

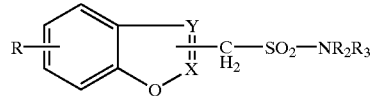

wherein R is hydrogen or a halogen atom, $R_2$ and $R_3$ are the same or different and are each hydrogen or a straight or branched alkyl having 1 to 3 carbon atoms, and one of X and Y is a carbon atom and another is a nitrogen atoms, provided that the methanesulfonamide group is bonded to the carbon atom of either X and Y, exemplified by zonisamide.

18 Claims, 3 Drawing Sheets

FIG._1A — Diabetic Zonisamide 50 mg/kg Before and After (Group D - Week 4 to Week 5)

FIG._1B — Diabetic Untreated Single Dose Zonisamide 50 mg/kg Before and After (Group B - Week 5 to Week 6)

FIG._1C — Diabetic Zonisamide 50 mg/kg Before and After WITHDRAWAL (Group D - Week 5 to Week 6)

METHODS FOR TREATING NEUROPATHIC PAIN USING HETEROARYLMETHANESULFONAMIDES

This application claims the benefit of U.S. Provisional Application No. 60/153,939 filed Sep. 15, 1999, which is hereby incorporated herein by reference in its entirety.

FIELD OF THE INVENTION

The present invention relates to methods of treating neuropathic pain with heteroarylmethanesulfonamides.

References

Ahmad, S. N. and Miljanich, G. P., *Brain Research* 453:247–256 (1988).

Bennett, G. J. and Xie, Y.-K., *Pain* 33:87–107 (1988).

Bennett, J. P. et al., in *NEUROTRANSMITRER RECEPTOR BINDING*, pp. 61–89; Raven press, New York, N.Y. (1983).

Ben-Sreti, M. M., et al., *Eur. J. Pharmacol.* 90:385–391 (1983).

Contreras, E., et al., *Eur. J. Pharmacol.* 148:463–466 (1988).

Dixon, W. J., *Ann. Rev. Pharmacol. Toxicol.* 20:441–462 (1976).

Jadad, A. R., et al., *Lancet* 339:1367–1371 (1992).

Kenakin, T. P., in *PHARMACOLOGIC ANALYSIS OF DRUG-RECEPTOR INTERACTION*, Raven Press, New York, N.Y. (1987).

Kim, S. H. and Chung, J. M., *Pain* 50:355–363 (1992).

McCleskey, E. W., et al., *Proc. Natl. Acad. Sci. USA* 84:4327–31 (1987).

McGeer, P. L., et al., in *MOLECULAR NEUROBIOLOGY OF THE MAMMALIAN BRAIN*, Plenum Press, New York, N.Y. (1987).

Sher, E. et al., *FASEB J.* 5:2677–2683 (1991).

Sher, E. and Clementi, F., *Neuroscience* 42301–42307 (1991).

Yaksh, T. L., and Rudy, T. A., *Physiol. Behav.* 17:1031–1036 (1976).

Cesena R. M.; Calcutt N. A., *Neurosci Lett* (IRELAND) 262(2):101–4 (1999)

Malmberg A. B. and Yaksh T. L., *J. Pharmacol. Exp. Ther.* 263: 136–146 (1992).

BACKGROUND OF THE INVENTION

Chronic or intractable pain, as may occur in conditions such as bone degenerative diseases, AIDS, Reflex sympathetic dystrophy (RSD), and cancer, is a debilitating condition which is treated with a variety of analgesic agents, and often opioid compounds, such as morphine. This type of pain is classified as nociceptive and is experienced in response to potentially tissue-damaging thermal, mechanical or chemical energy impinging upon specialized nerve endings of A and C fibers. Thus pain is usually perceived in response to nociceptive signaling by the nervous system as a result of noxious stimuli.

A few examples of neuropathic pain syndromes without nociception, i.e., not in response to noxious external stimuli are: diabetic neuropathy; postparapalegia pain; postherpetic neuralgia; reflex sympathetic dystrophy; thalamic syndrome; nerve root avulsion pain; phantom limb pain; postthoracotomy pain; tic douloureux and arachnoiditis.

Neuropathic pain, then, is a particular type of pain that has a complex and variable etiology. It is frequently a chronic condition attributable to complete or partial transection of a nerve, trauma or injury to a nerve, nerve plexus or soft tissue, or other conditions, also including cancer, AIDS and idiopathic causes. Neuropathic pain is characterized by hyperalgesia (lowered pain threshold and enhanced pain perception) and/or by allodynia (pain from innocuous mechanical or thermal stimuli). The condition is progressive in nature. The hyperesthetic component of neuropathic pain does not respond to the same pharmaceutical interventions as do the more usual nociceptive forms of pain, and development of effective long-term treatment modalities has been problematic. Repeated C fiber stimulation results in increased spinal afferent processing which is probably related to the hyperalgesia and allodynia symptoms. Evidence points to a complex scenario in which continued C fiber stimulation leads to local spinal release of glutamate, which activates spinal N-methyl-D-aspartate receptors. This activation then leads to increased intracellular Ca and later to spinal formation of several intermediaries, including prostanoids and nitric oxide. Both intermediaries facilitate spinal processing of signals directly by increasing the release of spinal neurotransmitters, and lead to the facilitated state of hyper-responsive pain signaling that lacks true nociceptive stimulus.

Opioid compounds (opiates) such as morphine, while effective in producing analgesia for many types of nociceptive pain, are generally not effective for treating the progressive stages of neuropathic pain. Moreover, if somewhat effective, these compounds are known to induce tolerance in patients, so that increased doses are required to achieve a satisfactory analgesic effect. At high doses, these compounds produce side effects (such as respiratory depression) which can be life threatening. In addition, opioids can produce physical dependence in patients.

Calcium blocking agents, including a number of L-type calcium channel antagonists, were tested as adjunct therapy to morphine analgesia, and positive results were attributed to their direct effects on calcium availability, since calcium itself is known to attenuate the analgesic effects of certain opioid compounds (Ben-Sreti, et al., 1983). EGTA, a calcium chelating agent, is effective in increasing the analgesic effects of opioids. However, results from tests of calcium antagonists as adjunct therapy to other opioids have been contradictory; some L-type calcium channel antagonists have been shown to increase the analgesic effects of opioids, while others of these compounds have been shown to decrease opioid effects (Contreras, et al., 1988).

U.S. Pat. No. 5,364,842 and 5,587,454 describe the effectiveness of N-type calcium channel blocking omega-conopeptide compositions in certain animal models of pain, including neuropathic pain. However, these compounds, being peptides, are not easily administered orally, but rather may be administered into the cerebrospinal fluid or other areas of the spinal column. By contrast, zonisamide is a T- and L-type calcium channel blocker and tests in animals (see Examples) have shown oral activity.

The anticonvulsant agent gabapentin exhibits antihyperalgesic properties in animal models of neuropathic pain. Diabetic rats display increased nocifensive behavior (i.e. avoidance behavior of stimuli) during the formalin test of persistent chemical irritation to the paw, suggesting the presence of abnormal pain processing mechanisms. In a study based on formalin-evoked behavior in diabetic rats, they were shown to have increased flinching during the normally quiescent phase of the 5.0% formalin test. Gabapentin (50 mg/kg i.p. 30 min pre-test) suppressed flinching during phases 1 and 2 of the formalin test in both control and diabetic rats. The findings were interpreted as showing efficacy of gabapentin against abnormal sensory processing in diabetic rats and the possible benefit for treating painful diabetic neuropathy. Since gabapenitin is an approved drug for use in humans in epilepsy, it has also be used in treatment of neuropathic pain, but the rather high dosages required to obtain a therapeutic effect make it undesireable for treatment of certain segments (e.g. the elderly) of the patient population.

Gabapentin (1-(aminomethyl)cyclohexaneacetic acid) is structurally related to the neurotransmitter GABA (gamma-aminobutyric acid) but it does not interact with GABA receptors, nor is it converted metabolically into GABA or a GABA agonist, nor is it an inhibitor of GABA uptake or degradation. Gabapentin was tested in radioligand binding assays at concentrations up to 100 μM and did not exhibit affinity for a number of other common receptor sites, including benzodiazepine, glutamate, N-methyl-D-aspartate (NMDA), quisqualate, kainate, strychnine-insensitive or strychnine-sensitive glycine, alpha$_1$, alpha$_2$, or beta adrenergic, adenosine A$_1$ or A$_2$, cholinergic, muscarinic or nicotinic, dopamine D$_1$ or D$_2$, histamine H$_1$, serotonin S$_1$ or S$_2$, opiate mu, delta or kappa, voltage-sensitive calcium channel sites labeled with nitrendipine or diltiazem, or at voltage-sensitive sodium channel sites with batrachotoxinin A 20-alpha-benzoate (excerpt from Physicians Desk Reference (1999 PDR Supplement B) Edition monograph for Neurontin Capsules). In vitro studies with radiolabeled gabapentin have revealed a gabapentin binding site in areas of rat brain including neocortex and hippocampus. although the identity and function of this binding site remain to be elucidated.

The heteroaryl methanesulfonamides of the invention are described in U.S. Pat. No. 4,172,896, which is hereby incorporated herein by reference. The active compounds of the invention are described by the generic structure of formula I

Formula I wherein R is hydrogen or a halogen atom, R$_2$ and R$_3$ are the same or different and are each hydrogen or a straight or branched alkyl having 1 to 3 carbon atoms, and one of X and Y is a carbon atom and another is a nitrogen atoms, provided that the methanesulonamido group is bonded to the carbon atom of either X and Y.

Compounds of the formula have a biochemical profile that includes inhibition of GABA release, sodium channel blockade, blockade of L- and T-type calcium channels and free-radical scavenger activity. The compounds are best characterized in vivo as anti-convulsants, and the compound given the generic name, zonisamide is used in the treatment of epilepsy in humans. Zonisamide has the chemical structure of 1,2-benzisoxazole-3-methanesulfonamide. Additionally, zonisamide is further described in the Merck Index (11$^{th}$ Ed.) at monograph no. 10094. It is the unexpected finding of the present invention that compounds of formula I reduce the severity of neuropathic pain in mammals.

SUMMARY OF THE INVENTION

The invention relates to methods for the treatment of neuropathic pain in mammals which comprises administering to a mammal in need of such treatment an efficacious amount of a compound of formula I Formula I wherein R is hydrogen or a halogen atom, R$_2$ and R$_3$ are the same or different and are each hydrogen or a straight or branched alkyl having 1 to 3 carbon atoms, and one of X and Y is a carbon atom and another is a nitrogen atoms, provided that the methanesulonamido group is bonded to the carbon atom of either X and Y.

A halogen atom is defined as fluorine, chlorine, bromine or iodine. Alkyl is defined as a straight or branched chain of carbon atoms connected by single bonds. Other terms in the description not defined herein have the standard meaning ascribed to them by one of skill in the relevant art.

Preferably the compound is 1,2-benzisoxazole-3-methanesulfonamide (zonisamide).

The compound may be administered in the range of 1 mg/kg to 400 mg/kg per day through a variety of routes of administration, including oral, topical, rectal, injection, or implantation. A preferred route of administration is via oral dosing.

The compounds of formula I may be used in treating a variety of neuropathic disorders, including: diabetic neuropathy, neuropathy secondary to nerve trauma, trigeminal neuralgia, post herpetic neuralgia, reflex sympathetic dystrophy, cancer pain and AIDS-related neuropathy.

These and other objects and features of the invention will become more fully apparent when the following detailed description of the invention is read in conjunction with the accompanying drawings.

DETAILED DESCRIPTION OF THE INVENTION

I. The Active Compounds of the Invention, Including Zonisamide, are Encompassed by Formula I Formula I wherein R is hydrogen or a halogen atom, $R_2$ and $R_3$ are the same or different and are each hydrogen or a straight or branched alkyl having 1 to 3 carbon atoms, and one of X and Y is a carbon atom and another is a nitrogen atoms, provided that the methanesulonamido group is bonded to the carbon atom of either X and Y.

Preclinial studies have shown that zonisamide has a non-classical pattern of activity in animal seizure models, and clinical studies have shown its efficacy against epilepsies that are resistant to classical antiepileptics.

Zonisamide has been found to block T-type calcium channels, which are likely to be present on the dorsal root ganglion and spinal cord dorsal horn neurons. Additionally it may promote GABA (γ-aminobutyric acid, a neurotransmitter) release under physiological or pathophysiological conditions. Since painful peripheral neuropathy is likely to be associated with a deficiency of the GABAergic inhibitory modulation that is normally engaged by pain input, this may advantageously affect neuropathic pain.

Zonisamide has also been found to ameliorate neuronal injury due to ischemia. NMDA receptor blockers (such as MK-801, dizocilpine) have proven efficacy against peripheral neuorpathies. It also has free-radical scavenger properties which can protect against such injuries in certain types of nerve injury, for example, diabetic neuropathy and nerve crush or trauma and progression of neuropathic disease.

II. Treatment of Neuropathic Pain

A. Neuropathic Pain

In general, while brain pathways governing the perception of pain are still incompletely understood, sensory afferent synaptic connections to the spinal cord, termed "nociceptive pathways" have been documented in some detail. In the first leg of such pathways, C- and A-fibers project from peripheral sites to the spinal cord and carry nociceptive signals. Polysynaptic junctions in the dorsal horn of the spinal cord are involved in nociceptive. processing and in the relay of sensations of pain to various regions of the brain. Analgesia, or the reduction of pain perception, can be effected directly by decreasing transmission along such nociceptive pathways.

Modulation of nociception is achieved by neural pathways descending from the cortex and hypothalamus to the mesencephalic central grey region, medullary reticular formation, and ultimately, the dorsal horn of the spinal cord. Analgesic opiates are thought to act by mimicking the effects of endorphin or enkephalin peptide-containing neurons, which synapse presynaptically at the C- or A-fiber terminal and which, when they fire, inhibit the release of neurotransmitters, including substance P, excitatory amino acids and calcitonin gene-related peptide (CGRP), and so down regulate nociceptive signaling. Descending pathways from the brain are also inhibitory on C- and A-fiber firing.

Presently, many postulates on the genesis of chronic pain incorporate the development of central (in addition to peripheral) sensitization in the spinal dorsal horn that is postulated to result from plastic changes in the processing of sensory, particularly nociceptive, stimuli. Much evidence suggests that this central sensitization results, at least in part, from activation of glutamatergic receptors and of intracellular messengers to which these receptors are coupled (e.g., calcium, nitric oxide, arachidonic acid, protein kinase C, etc.). By acting singly or in combination, these mediators are thought to significantly contribute to the development of nociceptive-induced plasticity in the dorsal horn, and ultimately produce neuropathic pain through this facilitated state of nociceptive signaling.

While neuropathic pain is known to have a number of underlying etiologies, it is characterized by a distinct set of symptoms. As described in greater detail below, these can include enhanced sensitivity to innocuous thermal-mechanical stimuli, abnormal sensitivity to noxious stimuli, tenderness, and spontaneous burning pain. Neuropathic pain is also progressive in nature, in that it generally worsens over time. Known treatment methods treat the symptoms without necessarily lessening the underlying pathology.

Although the present invention should not be limited by a particular theory of underlying mechanism, it has been observed that chronic neuropathic pain in humans is accompanied by changes in excitability of primary nociceptive afferents. This phenomenon is known as "nociceptor sensitization" and is characterized by increased excitability of the afferents to normally subthreshold stimuli. It is the discovery of the present invention that treatment with the compounds of the invention inhibit this phenomenon.

In accordance with the present invention, the compounds useful in treating neuropathic pain are also effective in preventing its progression. Such "neuropatholytic" properties may owe to its properties as a free radical scavenger and its calcium channel blocking activities. Zonisamide and analogs according to the formula I may also display neuroprotective properties which halt or slow further progression of the neuropathies, especially in diabetic neuropathy and traumatic neuropathy where free radicals and glutamate toxicity play key roles in disease progression.

B. Treatment Methods

While the present invention is not intended to be limited by adherence to any particular theory of underlying mechanism, one theory which is consistent with the invention is that acute nociception leads to alteration of signal transduction mechanisms in pain pathways. Under this theory, interference with such signal transduction prevents this alteration.

The compounds of the present invention can be by any of the accepted modes of systemic administration for agents which affect the central nervous system (CNS) including oral, parenteral, rectal, and otherwise systemic routes of administration. Any pharmaceutically acceptable mode of administration can be used, including solid, semi-solid, or liquid dosage forms, such as for example, tablets, suppositories, pills, capsules, powders, liquids suspensions, or the like, preferably in unit dosage form suitable to single administration of precise dosages, or in sustained or controlled release forms for the prolonged administration of the compound at a predetermined rate. The compositions will typically include a conventional pharmaceutical carrier or excipient and an active compound of formula I thereof and, in addition, may include other medicinal agents, pharmaceutical agents, carriers, adjuvants, etc. The compositions are advantageously compounded into unit dosage forms, containing a predetermined, standard amount of the active compound, to make dosing and patient compliance simpler.

The amount of active compound administered will course be dependent of the subject being treated, the severity of the affliction, the manner of administration and the judgment of the prescribing physician. However, an effective dosage is in the range of 1 mg/kg/day to 400 mg/kg/day, preferably 25–250 mg/kg/day.

For solid compositions, conventional non-toxic carriers include, for example mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol as a carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like to thereby form a solution or suspension. If desired, the pharmaceutical composition to be administered may also contain minor amounts of non-toxic auxiliary pH buffering agents and the like, for example, sodium acetate, sorbitan monolaurate, triethanolamine oleate, etc. Actual methods of preparing such dosage forms are known, or will be apparent to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount effective to alleviate the symptoms of the subject being treated.

Dosage forms or compositions containing active ingredient of formula I in the range of 0.25 to 95% with the balance made up from non-toxic carrier may be prepared. For oral administration, a pharmaceutically acceptable non-toxic composition is formed by the incorporation of any of the normally employed excipients, and may contain 1%–95% active ingredient, preferably 5%–50%.

Parenteral administration is generally characterized by injection, whether subcutaneously, intramuscularly, or perineurally. Injectables can be prepared in conventional forms, either as liquid solutions or suspension, solid forms suitable for solution or suspension in liquid prior to injection, or as emulsions. Suitable excipients include, for example, water, saline, aqueous dextrose, glycerol, ethanol or the like. In addition, if desired, the pharmaceutical compositions may also contain minor amounts of non-toxic substances such as wetting or emulsifying agents, auxiliary pH buffering agents and the like, for example, sodium acetate, sorbitan monolaurate, triethanolamine oleate, etc.

The percentage of active compound contained in such parenteral compositions is highly dependent on the specific nature thereof, as well as the activity of the compound and the needs of the subject, However, percentages of active ingredient of 0.1% to 10% in solution are employable, and will be higher if the composition is a solid which will be subsequently diluted to the above percentages. Preferably the composition will comprise 0.2–2% of the active agent in solution.

Other modes of administration can also be practiced in accordance with the present invention. For example, intravenous, intramuscular, and subcutaneous delivery are examples of delivery methods that are contemplated by the present invention. For direct application therapeutic compounds of the invention can be administered perineurally. Perineural administration can be by topical means, either directly or with the use of a transdermal applicator. Alternatively, perineural administration may be effected by subdermal injection. The resulting blockade of calcium channels reduces the heightened sensation produced by transmission through the neurite proliferation. Perineural delivery may also be effected by forming a cuff around the damaged nerve, preferably of a biodegradable matrix which includes a therapeutic N-type calcium channel blocking compound. Alternatively or in addition, the therapeutic compound can be placed in close proximity to the damaged nerve by conjugating the compound to or coating the compound on a nerve splint designed for repairing damaged nerves. Examples of such nerve splints are provided by U.S. Pat. No. 4,534,349 and 4,920,962.

Perineural delivery may also be effected by incorporating an active compound of formula I into suture materials, and using these materials to suture damaged tissues. This method is particularly useful for delivery of compound in areas where it is desirable to provide for inhibition of progression of neuropathy concomitant to tissue damage. U.S. Pat. No. 5,308,889 describes a collagen-based suture material that may be suitable for use for therapeutic delivery of the compounds.

One means for delivering the active compound to perineural sites is transdermal delivery. This form of delivery can be effected according to methods known in the art. Generally, transdermal delivery involves the use of a transdermal "patch" which allows for slow delivery of compound to a selected skin region. Although such patches are generally used to provide systemic delivery of compound, in the context of the present invention, such site-directed delivery can be expected to provide increased concentration of compound in selected regions of neurite proliferation. Examples of transdermal patch delivery systems are provided by U.S. Pat. No. 4,655,766 (fluid-imbibing osmotically driven system), and U.S. Pat. No. 5,004,610 (rate controlled transdermal delivery system).

Transdermal delivery may be carried using iontophoretic methods, such as described in U.S. Pat. No. 5,032,109 (electrolytic transdermal delivery system), and in U.S. Pat. No. 5,314,502 (electrically powered iontophoretic delivery device).

For transdermal delivery, it may be desirable to include permeation enhancing substances, such as fat soluble substances (e.g., aliphatic carboxylic acids, aliphatic alcohols), or water soluble substances (e.g., alkane polyols such as ethylene glycol, 1,3-propanediol, glycerol, propylene glycol, and the like). In addition, as described in U.S. Pat. No. 5,362,497, a "super water-absorbent resin" may be added to transdermal formulations to further enhance transdermal delivery. Examples of such resins include, but are not limited to, polyacrylates, saponified vinyl acetate-acrylic acid ester copolymers, cross-linked polyvinyl alcohol-maleic anhydride copolymers, saponified polyacrylonitrile graft polymers, starch acrylic acid graft polymers, and the like. Such formulations may be provided as occluded dressings to the region of interest, or may be provided in one or more of the transdermal patch configurations described above.

For delayed release, the compounds of the invention may be included in a pharmaceutical composition for formulated for slow release, such as in microcapsules formed from biocompatible polymers or in liposomal carrier systems according to methods known in the art.

For continuous release of active agent, the compound of formula I may be covalently conjugated to a water soluble polymer, such as a polylactide or biodegradable hydrogel derived from an amphipathic block copolymer, as described in U.S. Pat. No. 5,320,840. Collagen-based matrix implants, such as described in U.S. Pat. No. 5,024,841, are also useful for sustained delivery of therapeutics. Also useful, particularly for subdermal slow-release delivery to perineural regions, is a composition that includes a biodegradable polymer that is self-curing and that forms an implant in situ, after delivery in liquid form. Such a composition is described, for example in U.S. Pat. No. 5,278,202.

The method of the invention also includes local administration of the active compound to those regions of the spinal cord, such as to dorsal horn regions at affected vertebral levels, where polysynaptic relay of pain sensation occurs. This type of local application can be effected by intrathecal administration. Intrathecal administration delivers compound directly to the sub-arachnoid space containing cerebral spinal fluid (CSF). While effective, this method requires precise technical expertise to ensure delivery to the correct spot.

It is appreciated that delivery to spinal cord regions can also be by epidural injection to a region of the spinal cord exterior to the arachnoid membrane. It is further appreciated that it may be advantageous to add to the composition of the active ingredient means for enhancing permeation of the active through meningeal membranes. Such means are known in the art and include liposomal encapsulation, or addition of a surfactant or an ion-pairing agent to the peptide composition. Alternatively, or in addition, increased arachnoid membrane permeation can be effected by administering a hypertonic dosing solution effective to increase permeability of meningeal barriers.

The compounds of formula I can also be administered by slow infusion. This method is particularly useful, when administration is via the intrathecal or epidural routes mentioned above. Known in the art are a number of implantable or body-mountable pumps useful in delivering compound at a regulated rate. One such pump described in U.S. Pat. No. 4,619,652 is a body-mountable pump that can be used to deliver compound at a tonic flow rate or at periodic pulses. An injection site directly beneath the pump is provided to deliver compound to the area of need, for example, to the perineural region.

Efficacy of the foregoing methods of treatment are conveniently measured in the paw withdrawal test, or the formalin test described in Examples 1 and 2 below. In these models of peripheral neuropathy, it has been observed that neuropathic pain progressively increases over time after the nerve insult, with a plateau of pain response thereafter. To measure ability of a compound to prevent such progression, in the formalin model, the test compound is given just before or during the nerve insult, and threshold pain responses are measured thereafter. In the induced diabetic neuropathy model, comparisons are made in reduction of pain response against a control group of animals, not having streptozotocin-induced diabetes. Prevention of progression of neuropathic pain is observed when there is a heightened threshold to pain stimulus or where there is a prolongation of time to plateau, as compared to control animals. Efficacious dosages and formulations determined in these models are extrapolated to equivalent large animal and human dosages, according to methods known in the art, it being understood that such dosages vary according to the route of administration and by the responsiveness of the individual treated. Adjustment of dosages in view of such variables is within the skill of the ordinary administering physician.

C. Therapeutic Indications

As stated above, neuropathic pain may result from a number of separate etiologies. Generally, progression of such pain may be treated according to any of the methods described herein. However, in many cases it will be preferable to treat the pain in a manner that addresses its specific source. For example, when the pain is traceable to injury of a particular nerve fiber, it may be appropriate to treat such pain either by perineural application of compound to the affected nerve or by dermal application of compound to the affected region.

While a discussion of specific formulations and modes of delivery can be found in foregoing Sections this section sets forth some exemplary indications for which treatment according to the methods of the present invention may have particular therapeutic utility. The indications described below are by no means exhaustive, but are presented to illustrate some of the various therapeutic situations in which compounds according to formula I, and particularly zonisamide, can be used.

i. Ophthalmic indications. The eye is a heavily innervated organ. The cornea in particular is heavily innervated with C-fibers, containing an estimated 3–4000 fiber endings per $mm^2$ compared to an estimated 3–600 fiber endings per $mm^2$ of skin. Injury of the nerve fibers can lead to neuropathic pain of ophthalmic origin. In accordance with the present invention, the eye may be treated, preferably topically, with compounds according to formula I and particularly with zonisamide, to prevent progression of neuropathy. Application of compound may be achieved by topical administration to the eye, or, in more severe cases, by means of suprachoroidal administration. Such administration may be conveniently achieved by providing a suprachoroidal implant which includes, for example,. zonisamide. U.S. Pat. No. 5,164,188 describes a biodegradable implant that is suitable for chronic and controlled administration of compound to the suprachoroidal space. Chronic implanted therapeutics are also indicated after ophthalmic surgery, such as after surgery for detached retina or macular holes, where nerve damage may result.

ii. Dental indications. Delivery of the active compounds of formula I to regions of dental repair, such as endodontic repair concomitant to a root canal procedure, may be desirable as a means of preventing progression of dental neuropathy. Here, the therapeutic compound may be included in or added to one or more of the polymer based materials or resins inserted into the root canal after removing the pulp from the region, in accordance with standard techniques known in the art.

iii. Burn injury. Burn injuries are characterized by primary hyperalgesia to thermal and mechanical stimuli. In accordance with the principles discussed above, treatment of burned regions with compounds according to formula I may reduce progression of the hyperalgesic response by interfering with signal transduction mechanisms of nociceptor sensory receptors. In this embodiment of the invention, the therapeutic compound can be applied directly to the affected regions, or can be applied in a formulation that includes a protective biopolymer matrix, such as an artificial skin matrix.

iv. Reflex sympathetic dystrophy (RSD). RSD is thought to be due to abnormalities in the peripheral nervous system, and more particularly, to sensitization of cutaneous somatosensory afferents. Sympathetic outflow is thought to activate foci of ectopic neural hyperexcitability. Treatment of this condition to prevent its progression may be effected by any of the various dermal (topical) or subdermal routes of delivery discussed above. Perineural delivery may also be indicated for this condition.

v. Post-herpetic neuralgia. Post-herpetic neuralgia is characterized, in its acute phase, by intraneural inflamination which can cause damage to primary afferent axons. This damage may result in abnormal sensitivity to cutaneous stimuli. In general, the mode of treatment to prevent progression of abnormal sensitivity will depend on the location in the body of the affected nerve(s). Perineural or topical delivery of therapeutic N-type calcium channel blocking compound is indicated in this condition.

vi. Diabetic neuropathy. Neuropathy of primary afferent axons in long nerves is found in diabetic patients. This results in the dying-back and attempted regeneration of distal tips of primary afferent axons of these nerves. Nociceptor sensitization may ensue. Such sensitization and its progression may be treated according to one or more of the treatment methods described herein. In particular, perineural or topical application of therapeutic compound will be indicated, in accord with the location of the affected nerve and nerve beds.

vii. Arthritis. Arthritis is characterized by enhanced sensation of pain via articular afferents. The compounds of formula I find utility in treatment of such pain according to the principles set forth in the present invention. Generally, in treating articular afferents, therapeutic compound will be administered perineurally, including topically, in the vicinity of the affected joint.

D. In vivo Measurements of Neuropathic Analgesia.

Relief of neuropathic pain is conveniently measured in one or more of a number of animal models known in the art, in which an animal's response to a given pain stimulus is measured following experimental production of neuropathy. Inhibition of progression of the neuropathic condition can also be measured in this model, when measurements are taken in individual animals over time following the experimental neuropathic insult. While normal progression of the condition will be expected to result in animals that are increasingly sensitive to a given pain stimulus over time, inhibition of this progression will be observed as a leveling or diminishing of response to pain stimulus with time.

E. Dosages and Formulations

From the foregoing, it can be appreciated that treatment with the compounds of formula I and, more particularly, zonisamide (1,2-benzisoxazole-3-methanesulfonamide) are useful in preventing progression of neuropathic pain. Generally, dosages and routes of administration of the compounds will be determined according to the type or etiology or the pain and the size of the subject, according to standard pharmaceutical practices.

Intrathecal administration, introduction of material for diffusion throughout the subarachnoid space by means of lumbar puncture, either as a bolus dosage or as a constant infusion, can be used for treatment and prevention of progression of neuropathic pain. It is also appreciated that compound can be administered perineurally, for example by topical or subdermal application to cutaneous regions having affected nerve endings, according to methods known in the art. In addition, administration may by epidural means maybe employed. Epidural injection is administration upon (or outside) the dura mater of the spinal cord, through which the drug compound must permeate.

The following examples are intended to illustrate various characteristics of the method of the invention, but are in no way intended to limit the scope of the invention.

EXAMPLE 1

Effect of Zonisamide on Mechanical Hyperalgesia as Measured by Paw Withdrawal Latency in Rats with Streptozotocin (STZ)-Induced Diabetes Mellitus and Consequent Diabetic Neuropathy Male Wistar rats (250–300 g), following an overnight fast, were made diabetic with 55 mg/kg i.p. streptozotocin (Sigma, St. Louis, Mo., USA). Tail ven blood was sampled 48 h later and glucose estimated by reflectance photometry (Reflocheck, Boehringer Mannheim). All STZ-treated rats had blood glucose >15 mmol/l and were included in the study. Animals were housed in boxes of three or four and maintained with food and water ad libitum for up to 6 weeks. non-diabetic control rats were housed in identical conditions. Each week (Friday) paw—pressure latency was measured as described immediately below.

A force was applied at a constant rate with a cone-shaped piston to the upper surface of the rat hindpaw until paw withdrawal; the force triggering withdrawal is measured as the "paw withdrawal force". An arbitrary cut-off force of 240 g was adopted to preclude traumatic damage. Rats are trained such that latency is measured weekly, on Fridays.

At the start of week 5, drug treatments as defined for each of the groups set out below were commenced, such that 5 treatments preceded paw pressure testing. The injections and pressure test were timed so that, for each rat, the pressure test was made between 30 and 35 min after injection.

Groups (number of rats in each group=10)

A. Non-diabetic rats untreated with any agents

B. Diabetic untreated

C. Diabetic given zonisamide at 20 mg/kg p.o. for the final 5 days

D. Diabetic given zonisamide at 50 mg/kg p.o. for the final 5 days

E. Diabetic given MK-801* at 0.1 mg/kg i.p. for the final 5 days

[* MK-801 is dizocilpine, a non-competitive NMDA receptor antagonist (Merck Index, 11$^{th}$ Ed. monograph no. 3392) identified as a neuroprotective agent]

The schedule was maintained as follows:

Monday of week 1 the rats were injected with streptozotocin and blood glucose determinations were made Wednesday of that week, on the Friday the 1$^{st}$ paw pressure test was performed. In weeks 2, 3, and 4 only paw pressure tests were performed on each of the Fridays. In week 5 treatments of groups C, D and E were begun with either zonisarnide (Groups C and D) or MK-801 (Group E) and paw pressure tests were performed on all groups on Friday.

Further, Groups B and D were maintained for a 6$^{th}$ week as follows:

Group B was given a single dose of zonisamide at 50 mg/kg on the Friday of week 6 and paw withdrawal force measured 30 min later.

Group D was maintained without treatment for week 6 (drug "washout") and measured again on the Friday of week 6.

TABLE I

Paw Withdrawl Latencies In All Rats (threshold force in g).

| Group: | Week 1 Mean | SD* | Week 2 Mean | SD | Week 3 Mean | SD |
|---|---|---|---|---|---|---|
| A. Control Untreated | 219.3 | 8.4 | 221.2 | 11.8 | 228.8 | 7.6 |
| B. Diabetic Untreated | 213.3 | 10.2 | 207.1 | 6.3 | 200.5 | 6.9 |
| C. Diabetic zonisamide 20 mg/kg | 212.2 | 9.5 | 206.4 | 7.9 | 199.6 | 8.0 |
| D. Diabetic zonisamide 50 mg/kg | 212.72 | 10.3 | 208.9 | 10.2 | 200.7 | 7.2 |

TABLE I-continued

Paw Withdrawl Latencies In All Rats (threshold force in g).

| Diabetic MK-801 0.1 mg/kg | 214.9 | 10.0 | 207.1 | 11.2 | 200.0 | 8.7 |

| Group: | Week 4 Mean | SD | Week 5 Mean | SD | Week 6 Mean | SD |
|---|---|---|---|---|---|---|
| A. Control Untreated | 231.8 | 6.6 | 230.8 | 6.6 | | |
| B. Diabetic Untreated | 190.0 | 6.5 | 198.2 | 5.5 | 213.6 | 8.1 |
| C. Diabetic zonisamide 20 mg/kg | 190.0 | 9.4 | 195.0 | 6.4 | | |
| D. Diabetic zonisamide 50 mg/kg | 191.5 | 7.7 | 214.9 | 9.8 | 186.2 | 8.2 |
| Diabetic MK-801 0.1 mg/kg | 191.4 | 7.3 | 221.8 | 12.6 | | |

*Standard Deviation

Data are means with standard deviations. Zonisamide was given once daily (p.o.) between 08:30 and 09:00 for 5 days during Week 5. MK-801 was given at 0.1 mg/kg i.p. twice daily (morning and evening). All measurements were made on Fridays between 10:30 and 13:30 hr. In Week 6, the designated "diabetic untreated" group (Group B) was given a single p.o. dose of 50 mg/kg zonisamide 2–3 h before measurement. For Week 6, drug treatment was withdrawn from Group D (last dose on Friday of week 5).

Results

The mean values with standard deviations for paw withdrawal force are give, for animals of all 5 groups for each week, in Table 1.

Control untreated rats showed the usual modest learning effect over the first two weeks, associated with a slight rise in acceptable force ($p<0.005$; all cited p values are derived from paired t-tests). In contrast, diabetic rats showed reduced tolerance of force by 11% ($p<<0.0001$). Treatment with zonisamide at 20 mg/kg attenuated this hyperalgesia, but the reduction in tolerated force was still present and significant ($p<0.0002$). Treatment with zonisamide at 50 mg/kg obliterated the change in paw withdrawal force ($p=0.703$), indicating clear prevention of the hyperalgesia. MK-801 had a similar effect.

Treatment of previously untreated diabetic rats with zonisamide also obliterated the mechanical hyperalgesia ($p<<0.0001$) and withdrawal and washout of the drug after treatment with 50 mg/kg was associated with a return of the hyperalgesia of ($p<0.002$).

Figure 1A:
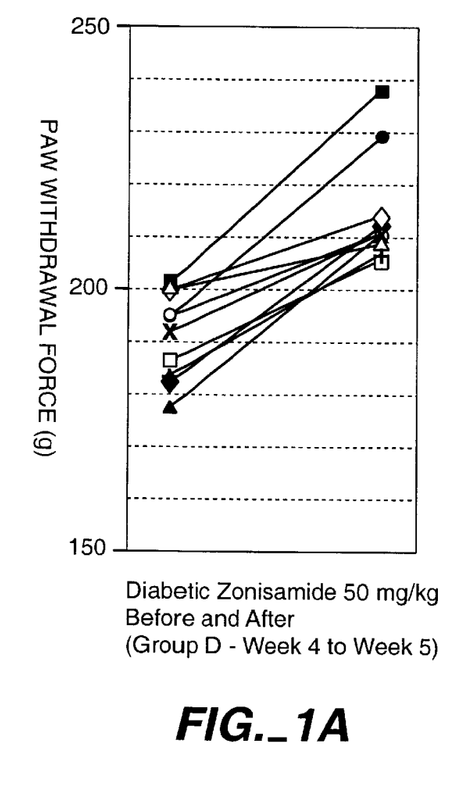
FIG. 1A illustrates the effect on the force required to cause a paw withdrawal response in each of the 10 test animals that were treated with zonisamide at 50 mg/kg daily for five days. Before and after measurements show the increase in force necessary to evoke a hyperalgesic pain response after treatment.
Figure 1B:
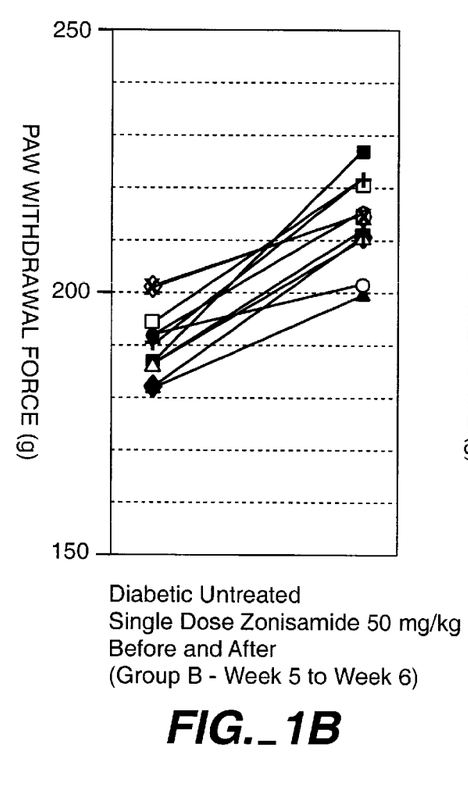
FIG. 1B illustrates a similar effect on the force required to cause a paw withdrawal response in each of the 10 test animals that were treated with a single 50 mg/kg dose of zonisamide Before and after measurements show the increase in force necessary to evoke a hyperalgesic pain response after treatment.
Figure 1C:
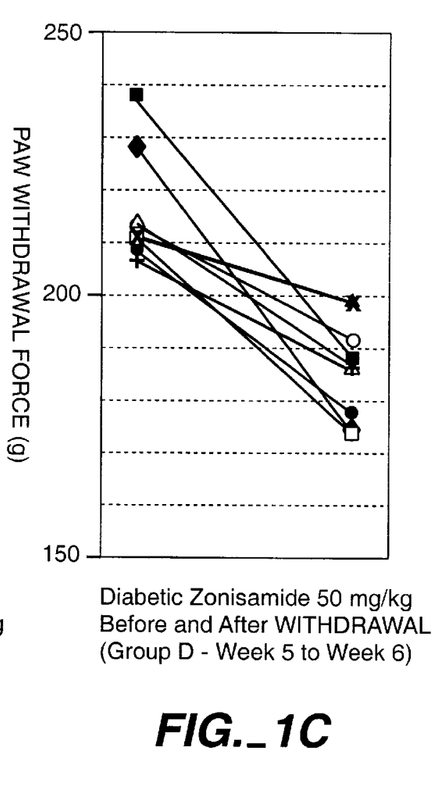
FIG. 1C illustrates the wash out effect on withdrawal of treatment with zonisamide. As the drug was cleared from the system, the force required to cause a paw withdrawal reaction was reduced, indicating a return to a hyperalgesic state.

These critical changes are shown for all rats in the FIG. 1A, 1B and 1C.

Conclusions

Zonisamide is active against the mechanical hyperalgesia associated with 4–5 weeks of STZ diabetes in rats. The activity appears to be dose related as illustrated by the complete obliteration of paw removal at the higher dosage studied.

The activity is present after a single dose, and is reversed as the drug leaves the system ("washes out").

EXAMPLE 2

The formalin test model in rats was conducted based on the protocol developed and reported by Malmberg A. B. and Yaksh T. L. (1992) as an animal model of hyperalgesia.

The formalin pain test produces an "early" pain that rapidly rises and falls in intensity during the first five minutes after the injection, followed by a "late" pain, which begins about 15 minutes after the injection and persists for about an hour. It has been observed that this formalin-induced pain continues even after the nerves carrying pain signals have been blocked which implies that long-lasting pain is determined not only by sensory stimulation during the discomfort but also by brain processes that persist without continual priming.

Eight (8) animals received 100 mg/kg zonisamide via oral (gastric lavage tube) administration, and eight (8) animals received sterile water as a vehicle. On the morning of testing, a small metal band (0.5 g) was loosely placed around the right hind paw. After 1 hour, the rat was placed in a cylindrical plexiglass changer for adaptation. After one additional hour, the rat was then placed in a similar cylindrical chamber that was placed on the sensing pad of an automated formalin device that senses the movement of the metal band in the space above the area above the pad. The formalin test involved injecting 50 µl of 5% formalin into the dorsal surface of the right hindpaw. Immediately thereafter, the animal displays flinging of the injected hindpaw. These flinches were counted automatically and continuously over the following one-hour interval. At one hour the animal was removed and sacrificed by carbon dioxide inhalation.

Results

Figure 2A:
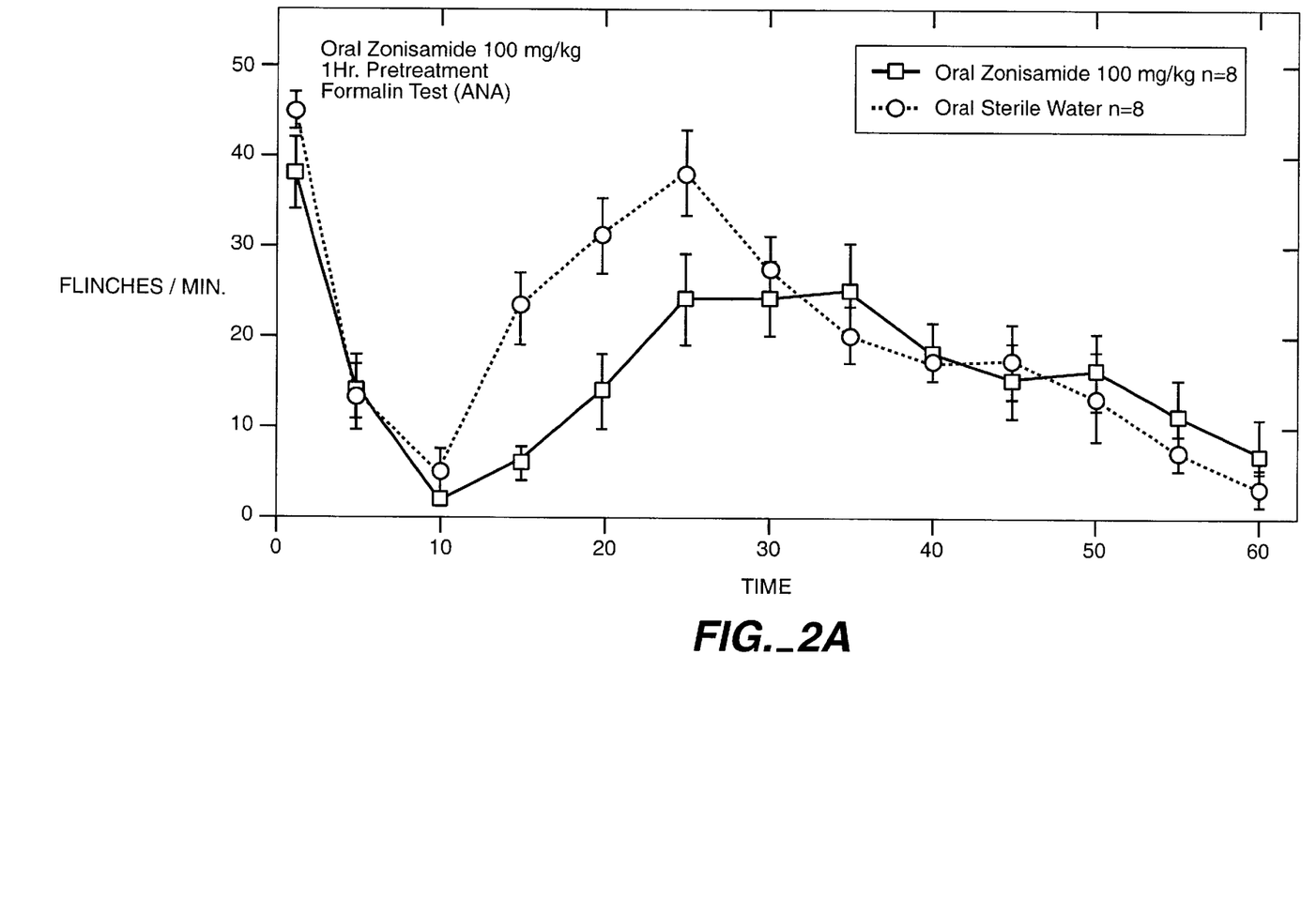
FIG. 2A is a comparative graph of the number of leg flinches per minute (grouped at minute intervals) over time for both test animals dosed with zonisamide at 100 mg/kg and control animals dosed only with water.
Figure 2B:
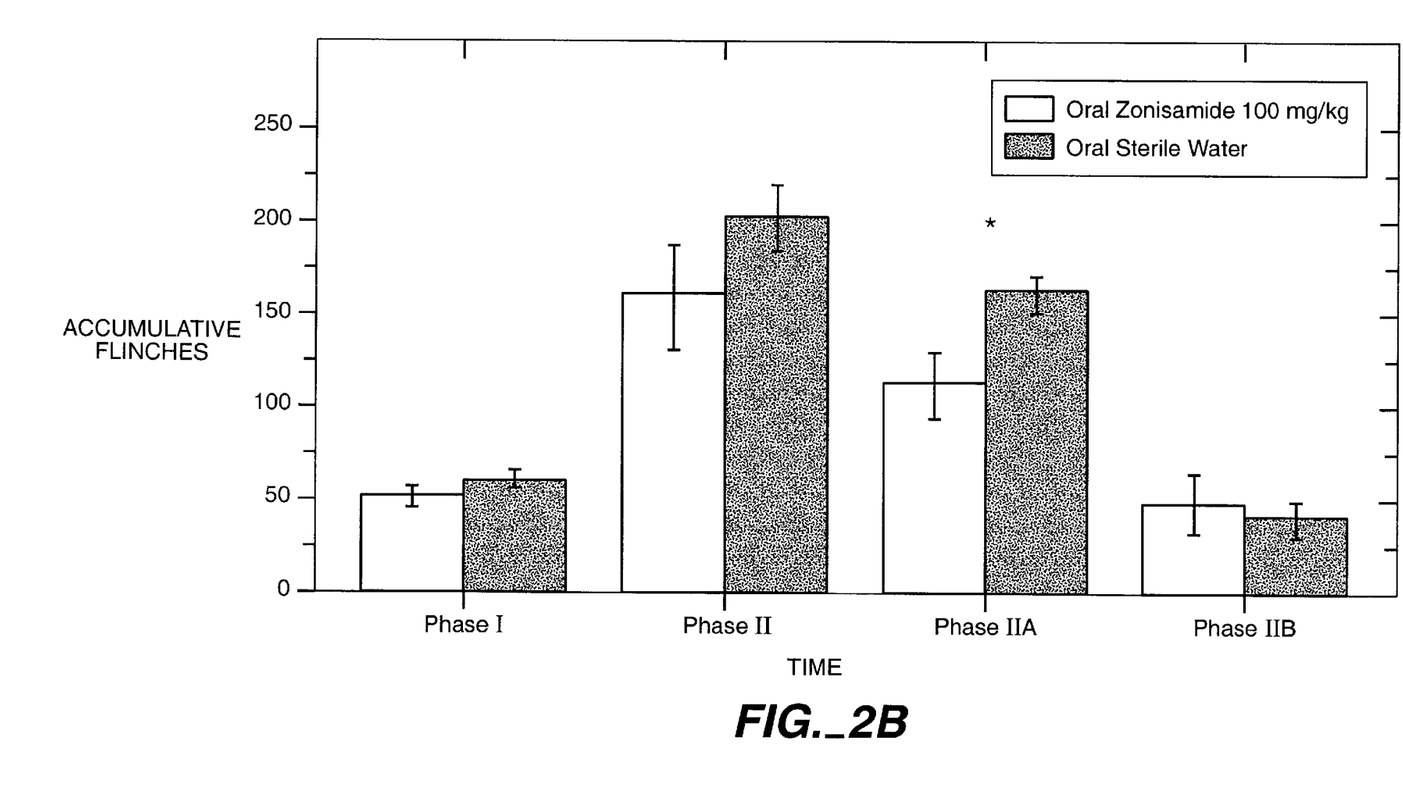
FIG. 2B is a cumulative bar chart of all flinches occurring during particular times (phases) after formalin injection. Phase IIA was significantly reduced in the group of rats treated with zonisamide.

The results of the tests are presented in FIGS. 2A as summations at 5-minute intervals, and in 2B broken down into phase responses. (Phase I being the "early" pain response to the formalin injection and phase II, IIA and IIB being "late" phase parts of the facilitated response state discussed above and in the Detailed Description).

Zonisamide was given orally I hour prior to testing at a dose of 100 mg/kg. At this dosage, there was not significant effect on Phase I, Phase II, or Phase IIB in this model. However, zonisamide did have a statistically significant effect on the Phase IIA of the Formalin model. No behavioral deficits were noted in the animals at this dosage level.

Conclusions

The lack of a Phase I effect suggests that the agent does not act in this model upon an acute component of the nociceptive processing, but the effect on Phase IIA is consistent with an action targeted at a facilitated state, and may also suggest a peripheral action of the agent greater than its central action.

Although the invention has been described with respect to particular embodiments, it will be apparent to those skilled that various changes and modifications can be made without departing from the invention. The scope of the invention should, therefore, be determined not with reference to the above description, but instead should be determined with reference to the appended claims along with the scope of their equivalents.

What is claimed is:

1. A method for the treatment of neuropathic pain in a mammal comprising administering to said mammal in need of such treatment an efficacious amount of a compound of formula I Formula I wherein R is hydrogen or a halogen atom, $R_2$ and $R_3$ are the same or different and are each hydrogen or a straight or branched alkyl having 1 to 3 carbon atoms, and one of X and Y is a carbon atom and another is a nitrogen atoms, provided that the methanesulfonamido group is bonded to the carbon atom represented by X or Y, provided the neuropathic pain is not trigeminal neuralgia.

2. The method of claim 1 wherein said compound is 1,2-benzisoxazole-3-methanesulfonamide zonisamide.

3. The method of claim 1 wherein the efficacious amount is in a range of 1 mg/kg to 400 mg/kg per day.

4. The method of claim 3 wherein the compound is administered orally.

5. The method of claim 4 wherein said method further comprises administering the compound in a unit dosage form.

6. The method of claim 1 wherein said administration is by perineural application.

7. The method of claim 1 wherein said the compound of formula I is administered topically to a skin region having or manifesting the neuropathic pain.

8. The method of claim 1 wherein the compound is administered orally.

9. The method of claim 1 wherein the neuropathic pain is selected from the group consisting of diabetic neuropathy, optic neuropathy, neuropathy secondary to nerve trauma, post herpetic neuralgia, reflex sympathetic dystrophy, cancer pain and AIDS-related neuropathy.

10. The method of claim 9 wherein said compound is 1,2-benzisoxazole-3-methanesulfonamide zonisamide.

11. The method of claim 10 wherein the efficacious amount of zonisamide is in a range of 1 mg/kg to 400 mg/kg per day.

12. The method of claim 11 wherein the compound is administered orally.

13. The method of claim 12 wherein said method further comprises administering the compound in a unit dosage form.

14. The method of claim 9 wherein said administration is by perineural application.

15. The method of claim 9 wherein said the compound is administered topically to a skin region having or manifesting the neuropatbic pain.

16. The method of claim 9 wherein the compound is administered orally.

17. A method for the treatment of neuropathic pain in a skin region of a mammal comprising, a transdermal patch providing an efficacious amount of a compound of formula I Formula I wherein R is hydrogen or a halogen atom, $R_2$ and $R_3$ are the same or different and are each hydrogen or a straight or branched alkyl having 1 to 3 carbon atoms, and one of X and Y is a carbon atom and another is a nitrogen atoms, provided that the methanesulfonarnido group is bonded to the carbon atom of either X and Y applied to the having or manifesting the neuropathic pain, provided that the neuropathic pain is not trigeminal neuralgia.

18. The method of claim 17 wherein the compound of formula I is zonisamide.

* * * * *

UNITED STATES PATENT AND TRADEMARK OFFICE
CERTIFICATE OF CORRECTION

PATENT NO. : 6,489,350 B1
DATED : December 3, 2002
INVENTOR(S) : Benedyk

It is certified that error appears in the above-identified patent and that said Letters Patent is hereby corrected as shown below:

Title page,
Item [73], Assignee, should read -- Eisai, Inc., Teaneck, NJ (US) --.

Column 15,
Line 2, change "nitrogen atoms," to -- nitrogen atom, --.
Lines 7 and 28, delete "1,2-benzisoxazole-3-methanesulfonamide".
Line 17, delete "said".

Column 16,
Line 6, delete "said".
Line 12, change "comprising," to -- comprising --.
Line 25, change "nitrogen atoms," to -- nitrogen atom, --.
Line 27, change "X and Y applied to the having" to -- X or Y; wherein the transdermal patch is applied to the skin region having --.

Signed and Sealed this

Third Day of January, 2006

JON W. DUDAS
*Director of the United States Patent and Trademark Office*